(12) United States Patent
Arnold et al.

(10) Patent No.: US 7,498,303 B2
(45) Date of Patent: Mar. 3, 2009

(54) GNRH ANALOGUES FOR TREATMENT OF URINARY INCONTINENCE

(75) Inventors: Susi Arnold, Moeriken (CH); Iris Reichler, Zurich (CH); Madeleine Hubler, Wernetshausen (CH)

(73) Assignee: University of Zuerich (CH)

( * ) Notice: Subject to any disclaimer, the term of this patent is extended or adjusted under 35 U.S.C. 154(b) by 190 days.

(21) Appl. No.: 10/415,519

(22) PCT Filed: Oct. 26, 2001

(86) PCT No.: PCT/CH01/00636

§ 371 (c)(1),
(2), (4) Date: Apr. 30, 2003

(87) PCT Pub. No.: WO02/36144

PCT Pub. Date: May 10, 2002

(65) Prior Publication Data

US 2004/0023878 A1 Feb. 5, 2004

(30) Foreign Application Priority Data

Oct. 30, 2000 (EP) .................................. 00811011

(51) Int. Cl.
*A61K 38/00* (2006.01)
*A61K 31/56* (2006.01)
*A01N 45/00* (2006.01)

(52) U.S. Cl. ........................................ 514/12; 514/171

(58) Field of Classification Search ...................... None
See application file for complete search history.

(56) References Cited

U.S. PATENT DOCUMENTS

| | | | | |
|---|---|---|---|---|
| 5,211,952 | A * | 5/1993 | Spicer et al. | 424/426 |
| 5,340,585 | A * | 8/1994 | Pike et al. | 424/426 |
| 5,340,805 | A * | 8/1994 | Harrington, Jr. | 514/176 |
| 5,434,136 | A * | 7/1995 | Mathias | 514/15 |
| 5,681,817 | A * | 10/1997 | Hodgen et al. | 514/12 |
| 5,789,442 | A * | 8/1998 | Garfield et al. | 514/561 |
| 6,028,106 | A * | 2/2000 | Garfield et al. | 514/561 |
| 6,051,558 | A * | 4/2000 | Burns et al. | 514/15 |
| 6,274,573 | B1 * | 8/2001 | Katsuki et al. | 514/179 |
| 6,337,318 | B1 * | 1/2002 | Trigg et al. | 514/15 |
| 6,416,778 | B1 * | 7/2002 | Ragavan et al. | 424/430 |
| 6,586,000 | B2 * | 7/2003 | Luo et al. | 424/449 |
| 6,652,874 | B2 * | 11/2003 | Ragavan et al. | 424/430 |
| 6,777,386 | B2 * | 8/2004 | Trigg et al. | 514/2 |
| 2003/0139433 | A1 * | 7/2003 | Aharony et al. | 514/269 |
| 2005/0197362 | A1 * | 9/2005 | Ishihara et al. | 514/317 |

FOREIGN PATENT DOCUMENTS

WO    WO 97/00693    * 1/1997

WO    WO 99/55358    11/1999

OTHER PUBLICATIONS

Committee for Veterinary Medicinal Products. Deslorelin acetate, summary report. (accesed online Oct. 5, 2005) Feb. 2002. pp. 1-3.*
Brigham and Women's Hospital. Medications for Urinary Incontinence. (accesed online Oct. 5, 2005). pp. 1-4.*
Harrington et al. Danazol for urinary incontinence in tropical spastic paraparesis. The Lancet. Feb. 8, 1992. vol. 339, p. 8789.*
Danazolumn (Danazol). Accessed online Apr. 4, 2006 at http://best-price-prescription-drugs.com/Danazolum.htm.*
Bachem AG / Deslorelin Acetate. Accessed online Apr. 13, 2006 at http://www.bachem.com/static/html/deslorelin-acetate-1__184__208.html.*
Conn et al. Gonadotropin releasing hormone and its analogs. N Eng J Med. 1991 vol. 324, No. 2, pp. 93-103.*
Moghissi. A Clinician's Guide to the Use of Gonadotropin-Releasing Hormone Analogues in Women. Medscape General Medicine 2(1), 2000. Posted online Feb. 10, 2000 at http://www.medscape.com/viewarticle/408909_print. pp. 1-10.*
H.J.C. Berendsen. A Glimpse of the Holy Grail? Science (1998) 282, pp. 642-643.*
Rudinger. In: Peptide Hormones, JA Parsons, Ed: (1976) 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, 9633-9637.*
D. Voet and J.G. Voet. Biochemistry, 2nd Edition.(1995), pp. 235-241.*
Janssens L. A. et al., Comparisons between stress incontinence in women and sphincter mechanism incompetence in the female dog; Veterinary Record vol. 141 (24): p. 620-625 (Dec. 13, 1997).
Conn P. M. et al., Gonadotropin-releasing hormone and its analogues; The New England Journal of Medicine 324 (2): p. 93-103, Massachusetts Medical Society, Waltham MA, US. 2 (Jan. 10, 1991); XP001002186.
International Search Report corresponding to International Application Serial No. PCT/CH01/00636 (dated Mar. 27, 2002) 4 pages.
Society, I.C. First report on the standardization of terminology of lower urinary tract function; Br J Urol 48: p. 39-42 (1976).
Hilton, P. and S.L. Stanton, Urethral pressure measurement by microtransducer: the results in symptom-free women and in those with geniune stress incontinence; Brit J Obstet Gynaecol vol. 90: p. 919-933 (Oct. 1983).

(Continued)

*Primary Examiner*—Cecilia Tsang
*Assistant Examiner*—Marcela M Cordero Garcia
(74) *Attorney, Agent, or Firm*—Joyce von Natzmer; Pequignot + Myers LLC

(57) ABSTRACT

The use of at least one GnRH analogue for the preparation of a medicament for the prevention and/or treatment of side effects of ovarectomy or symptoms associated with reproductive senescence in female mammals, in particular urinary incontinence, hot flushes, and skin/hair changes are disclosed.

18 Claims, No Drawings

OTHER PUBLICATIONS

Arnold, S., Harninkontinenz bei kastrierten Hündinnen: Bedeutung, Pathophysiologie und Behandlung. Vet special: p. 1-103 (book) (ed. Ferdinand Enke Verlag. 1997, Stuttgart).

Ballanger, P. and P. Rischmann, Female urinary incontinence; Eur Urol vol. 36: p. 165-174 (1999).

Colon, J. et al., Effects of contraceptive doses of the progestagen megestrol acetate on luteinizing hormone and follicle-stimulating hormone secretion in female dogs. J Reprod Fert, Supp 47: p. 519-521 (1993).

Arnold, S., et al., Incontinentia urinae bei der kastrierten Hündin: Häufigkeit und Rassedisposition. Schweiz Arch Tierheilk vol. 131: p. 259-263 (1989).

Hodgkinson, C.P. et al., Retropublic urethropexy or colposuspension; In: S.L. Stanton & E.A. Tanagho (ed): Surgery of female incontinence: p. 55-68 (Berlin: E.A. Springer Verlag, 1980) (book).

Holt, P.E.,Urinary incontinence in the bitch due to sphincter mechanism incompetence: surgical treatment. J Small Anim Pract vol. 26: p. 237-246 (1985).

Holt, P.E.,Long-term evaluation of colposuspension in the treatment of urinary incontinence due to incompetence of the urethral sphincter mechanism in the bitch, Vet Rec vol. 127: p. 537-542 (Dec. 1, 1990).

Wise, P.M., K.M. Krajnak, and M.L. Kashon, Menopause: The aging of multiple pacemakers. Science vol. 273: p. 67-70 (Jul. 5, 1996).

Ushiroyama, T., et al., Hypergonadotropinemia with estradiol secretion in peri- and post-menopausal period. Acta Obstet Gynecol Scand, vol. 139-143 (1989).

Sherman, B.M., J.H. West and S.G. Korenman, The menopausal transition: Analysis of LH,FSH, Estradiol and Progesterone Concentrations during menstrual cycles of older women. J Clin Endocrin Metab, vol. 42, No. 4: p. 629-636 (1976).

Lenton, E.A. et al., Inhibin concentrations throughout the menstrual cycles of normal, infertile, and older women compared with those during spontaneous conception cycles. J Clin Endocrinol Metabol vol. 73, No. 6: p. 1180-1189 (1991).

MacNaughton J. et al., Age related changes in follicle stimulating hormone, luteinizing hormone, oestradiol and immunoreactive inhibin in women of reproductive age. Clin Endocrinol vol. 36: p. 339-345 (1992).

Overlie, I., et al., The endocrine transition anround menopause—a five years prospective study with profiles of gonadotropines, estrogens, androgens and SHBG among healthy women. Acta Obstet Gynecol Scand vol. 78: p. 642-647 (1999).

Larson, B., A. Collins, and B.M. Landgren, Urogenital and vasomotor symptoms in relation to menopausal status and the use of hormone replacement therapy (HRT) in healthy women during transition to menopause. Maturitas vol. 28(2): p. 99-105 (1997).

Ushiroyama, T., K. Toyoda, and O. Sugimoto, Contribution of endocrine changes to depressive mood in peri- and post-menopausal women. Bulletin of the Osaka Medical College vol. 37(1, 2): p. 81-86 (1991).

Ushiroyama, T., et al., Evidence for attenuation of gonadotropin pulse frequency in hypergonadotropic women with estradiol secretion in the menopausal transition. Psychoneuroendocrinology vol. 24: p. 85-97 (1999).

Mohide, E.A., The prevalence and scope of urinary incontinence. Clinics in Geriatr. Med., vol. 2(4): p. 639-654 (1986).

Jolleys, J.V., Reported prevalence of urinary incontinence in women in a general practice. Br Med J. vol. 296: p. 1300-1302 (1988).

Versi, E., Incontinence in climateric. Clin Obstet Gynecol 33(2): p. 392-398 (Jun. 1990).

Herzog, A.R. and N.H. Fultz, Prevalence and incidence of urinary incontinence in community-dwelling population. J Am Geriatr Soc vol. 38(3): p 273-281 (1990).

Burgio, K.L. et al., Prevalence, incidence and correlates of urinary incontinence in healthy, middle-aged women, J Urol. vol. 146: p. 1255-1259 (Nov. 1991).

O'Connell, H.E., R.J. MacGregor, and J.M. Russell, Female urinary incontinence management in primary care, Med. J Aust vol. 157(8): p. 537-544 (Oct. 19, 1992).

Kuh, D., L. Cardozo, and R. Hardy, Urinary incontinence in middle aged women: childhood enuresis and other lifetime risk factors in a British prospective cohort. J Epidemiol Community Health vol. 53(8): p. 453-458 (1999).

Yarnell, J.W.G. and A.S. St.Leger, The prevalence, severity and factors associated with urinary incontinence in a random sample of the elderly. Age & Ageing vol. 8: p. 81-85 (1979).

Cervigni, M., Hormonal influences in the lower urinary tract. Female urology, Chapter 49: p. 539-559 (ed. S. Raz. 1996, Philadelphia: Saunders, W.B).

Rud, T., Urethral pressure profile in continent women from childhood to old age. Acta Obstet Gynecol Scand 59: p. 331-335 (1980).

Edwards, L. and J. Malvern, The urethral pressure profile: Theoretical considerations and clinical application. British J Urol vol. 46: p. 325-336 (1974).

Abrams, P, R.C.L. Feneley and M.Torrens. Klinischer Wert urodynamischer Untersuchungen. In: Urodynamic für Klinik und Praxis, Chapter 5: p. 126-186 (P. Abrams, R.C.L. Feneley and M.Torrens (eds.) 1987: Berlin: Springer-Verlag).

Misrahi, M., et al., The LH/CG and FSH receptors: different molecular forms and intracellular traffic. Molecular and cellular endocrinology vol. 125: p. 161-167 (1996).

Wasowicz, G., et al., Evidence for the presence of luteinizing hormone-chorionic gonadotrophin receptors in the pig umbilical presence cord. Journal of reproduction and fertility vol. 117: p. 1-9 (1999).

Tao, Y.-X., et al., The urinary bladder of a women is a novel site of luteinizing hormone-human chorionic gonadotropin receptor gene expression. Am J Obstet Gynecol. vol. 179(4): p. 1026-1031 (Oct. 1998).

Venencie, P.Y., et al., Luteinizing hormone/human chorionic gonadotrophin receptors in various epidermal structures. British Journal of Dermatology vol. 141: p. 438-446 (1999).

Hazum, E. and P.M. Conn, Molecular mechanism of gonadotropin releasing hormone (GnRH) Action. I. The GnRH Receptor. Endocrine Review vol. 9 (4): p. 379-386 (1988).

Cavitte, J.-C., et al., Reversible effects of long-term treatment D-TRP6-LH-RH-microcapsules on pituitary gonadal axis, spermatogenesis and prostate morphology in adolescent and adult dogs. Andrologia vol. 20: p. 249-263 (1988).

Lacoste, D., et al., Normal gonadal functions and fertility after 23 months of treatment of prepubertal male and female dogs with the GnRH agonist (D-Trp$_6$, des-Gly-NH$_2$10)GnRH etylamide. J Androl vol. 10(6): p. 456-465 (1989).

Lacoste, D., et al., Reversible inhibition of testicular androgen secretion by 3-, 5- and 6 month controlled release microsphere formulations of the LH-RH agonist (D-Trp6, des-Gly-NH102)LH-RH ethylamide in the dog. J Steroid Biochem vol. 33(5): p. 1007-1011 (1989).

Aspden, W.J., et al., Direct actions of the Luteinizing Hormone-Releasing Hormone Agonist, Deslorelin, on Anterior Pituitary contents of Luteinizing Hormone (LH) and Follicle-Stimulating Hormone (FSH), LH and FSH subunit messenger ribonucleic acid, and Plasma concentrations of LH and FSH in castrated male cattle. Biology of reproduction vol. 55: p. 386-392 (1996).

Roger, M., et al., Long term treatment of male and female precocious puberty by periodic administration of a long-acting preparation of D-Trp6-Luteinizing hormone-releasing hormone microcapsules. Journal of Clinical Endocrinology and Metabolism vol. 62(4): p. 670-677 (1986).

Okkens, A.C., et al., Evidence for prolactin as the main luteotrophic factor in the cyclic dog. The veterinary quarterly vol. 12(4): p. 193-201(1990).

Kobashi, K.C. and G.E. Leach, Stress urinary incontinence. Curr Opin Urol vol. 9(4): p. 285-290 (1999).

Glavind, K., A.L. Mouritsen, and G. Lose, Management of stress and urge urinary incontinence in women. Acta Obstet Gynecol Scand vol. 78: p. 75-81 (1999).

Reichler, I.M. et al, The effect of GnRH analogs on urinary incontinence after ablation of the ovaries in dogs. Theriogenology vol. 8840 pp. 1-10 (2003).

Reichler, I.M. et al, Effect of GnRH treatment and FSH Concentration in Female Dogs. Reproduction in Domestic Animals vol. 37(4) Abstract P1.107, p. 248 (Aug. 2002).

* cited by examiner

… … …

GNRH ANALOGUES FOR TREATMENT OF URINARY INCONTINENCE

CROSS REFERENCE TO RELATED APPLICATIONS

This application is a National Stage entry of International Application No. PCT/CH01/00636, filed Oct. 26, 2001 which claims benefit from European Application No. 00811011.6, filed Oct. 30, 2000.

TECHNICAL FIELD

The present invention provides pharmaceutical compositions for the prevention and treatment of side effects of ovarectomy or symptoms associated with reproductive senescence, especially urinary incontinence, as well as mood changes, skin changes, hair changes, vasomotor symptoms, especially hot flushes, in mammalian females, particularly in post menopausal women and in spayed bitches. Connected with such treatments is the prevention of urinary tract infections.

BACKGROUND OF THE INVENTION

If the endocrine activity of the gonads decreases or if the gonads are removed, women and dogs show similar changes. With the reproductive senescence in women, as well as after ovarectomy in the bitch, symptoms such as urinary incontinence, vasomotor symptoms, in particular hot flushes, changes of the mood, skin and hair increasingly occur. After ovarectomy, as well as at the beginning of the reproductive senescence, corresponding hormonal changes occur with a great increase in serum concentrations of FSH (Follicle stimulating hormone) and LH (Luteinising hormone).

1. Urinary Incontinence in General

Urinary incontinence is defined by the International Continence Society [1] as the objective demonstration of involuntary loss of urine consequent to bladder and/or urethral sphincter dysfunction.

If the anatomical conditions are normal, two different pathophysiological mechanisms can lead to urinary incontinence: an increased tone of the bladder with a normal closure function of the urethra, or an insufficient closure function of the urethra with a normal bladder pressure during the filling phase.

An insufficient closure function of the urethra plays a crucial role in both the urinary incontinence in bitches due to spaying and the stress incontinence in women [2] [3] [4].

2. Removal of the Ovaries (Spaying) in the Bitch

Side Effects

Gonadectomy can lead to side effects. The most common is urinary incontinence, which occurs in one in five spayed bitches. The continuous hair loss, which is due to the shortened life span of the hairs after spaying, can be disturbing to the owner. Less common, and mainly in particular breeds, is the excessive growth of the undercoat which leads to a "babycoat". If food is offered ad libitum the increased appetite can lead to adipositas and vulvapyodermia. In case of dominant bitches gonadectomy may increase aggressivity.

Endocrine Principles

Twice per year the bitch is on heat for about 3 weeks. Her seasonal mono-oestrous cycle is divided into 4 periods, anestrus, pro-oestrus, oestrus and metoestrus. During anoestrus the plasma concentrations of sexual steroids are very low. The level of progesterone is below 1 ng/ml, and that of estrogen is below 10 pg/ml. Towards the end of anoestrus, about four weeks before the onset of the next heat, slight increases in estradiol concentrations can be measured. At the onset of the heat, starting with pro-oestrus, the internal secretion of estradiol is slightly increased by the growing follicles. At the end of pro-oestrus a sudden increase of the internal estradiol secretion occurs over two to three days, resulting in a peak serum estradiol of 40 to 90 pg/ml. During the pro-oestrous period the follicular growth is stimulated by pulsatile FSH and LH release and 24 to 72 hours after the last LH-peak ovulation is triggered. The actual oestrus, which is characterized by the bitch's acceptance of the male dog, is dominated by an increasing serum progesterone concentration, whereas the estrogen level returns to basal concentrations of less than 10 pg/ml. The corpora lutea produce progesterone for about three months. The progesterone production is independent of whether the bitch is pregnant or not pregnant. The luteal phase is called metoestrus. After the luteolysis, serum progesterone levels are below 1 ng/ml, the bitch is in the period of ovarian quiescence, the anoestrus. During this period the average concentrations of the gonadotropins FSH and LH are about 114 ng/ml and 1.1 ng/ml respectively [5]

With gonadectomy the source of the sexual steroids estrogen and progesterone is removed and afterwards, they are only measurable in very low serum concentrations that are not different from those measured during anoestrus. As there is no longer a feed back mechanism, FSH and LH are secreted unhindered, resulting in average concentrations of 1086 ng/ml and 7.4 ng/ml respectively [5]

Relationship Between Endocrine Changes and Side Effects of Gonadectomy

Until now, the side effects of spaying have been explained as resulting from the missing estrogen secretion. But various observations do not agree with this hypothesis. In sexual intact bitches the endogenous estrogen concentration is elevated only for a short period only once or twice per year. In many bitches which are treated with depot gestagens for suppressing of the estrous cycle for years, the endogenous estrogen concentration is permanently reduced to basal levels. In these bitches with a permanently suppressed ovarian activity most of the side effects seen after spaying, in particular urinary incontinence, do not occur. If low estrogen concentrations would be responsible for the occurrence of urinary incontinence, it could be assumed that the replacement therapy with estrogens would be successful, but in fact, it is effective only in 65% of the cases [6]. Conversely, it would be expected that in sexually intact bitches urinary incontinence does not occur, especially not during the heat. Apart from the many incontinent bitches, due to spaying, seen as patients at the Department of Reproduction, University of Zurich, there are several intact bitches which are incontinent exclusively during estrus. Urodynamic data supports these observations, showing a significantly reduced urethral closure pressure under the influence of estrogens, during the estrus.

Urinary Incontinence of the Bitch

Urinary incontinence is the most common and embarrassing side effect of spaying for both the owner and the dog [3]. In all bitches gonadectomy leads to a significant reduction in the urethral closure pressure within one year. In 20% of the bitches the urethral closure pressure drops below the critical threshold value of 7.5 cm $H_2O$, leading to urinary incontinence [3]. Urinary incontinence also has medical consequences: Due to the lowered urethral closure function the ascension of bacteria, leading to an urinary tract infection, is enhanced. Additionally, the continuous contamination of the perineal region with urine can result in skin ulceration.

Therapy is aimed at improving the urethral closure pressure which can be achieved by conservative or surgical methods. First choice are alpha-adrenergic substances such as ephedrinhydrochloride or phenylpropanolamine, at 1.5 mg/kg BW p.o. two to three times per day. If these medications are given every 8 hours, continence was achieved in 74%, and at least 24% showed some improvement. But, for the owner it is not always possible to administer tablets this frequently. Side effects such as diarrhea, vomiting, anxiety and nervousness are observed only infrequently. Alpha-adrenergic substances are contraindicated in case of glaucoma, cardiac arrhythmia and progressive nephropathy. As an alternative therapy estrogens can be used, which improve the responsiveness of catecholamine receptors of the urethra. But given alone, their effectiveness is inferior to that of the alpha-adrenergic substances, for they were found ineffective in 24% of the cases [3]. The substitution with estrogens in dogs can lead to a bone marrow depression, which can be fatal. Quite a common side effect of the estrogen therapy is recurrence of heat-like symptoms and with it sexual attractiveness to male dogs. These side effects can even be observed after therapy with phytoestrogens.

If therapy with medication is unsuccessful, too much trouble to the owner, accompanied with side effects, or even contraindicated, a surgical or endoscopic procedure can be considered. The injection of collagen into the submucosa of the proximal urethra, under endoscopic control, is successful in 75% of the cases and can be repeated if necessary. But this therapy requires a full anesthesia, it is expensive and its success is dependent on the experience of the surgeon. Even more invasive, and therefore expensive, is a surgical method, the classical retropubic urethropexy for incontinent women [7] which has been adapted for dogs [8]. This colposuspension, which is performed in full anesthesia after laparotomy, is only effective in 53% of the dogs with continence [9].

3. Reproductive Senescence in Women

Occurrence

Declining reproductive function is an inevitable part of the aging process [10]. The dramatic endocrine changes brought about by reproductive senescence have biological, social and cultural implications that profoundly influence the latter half of a woman's life.

Symptoms

Women may experience a number of symptoms such as hot flushes, mood changes and altered sleep pattern during the transition from the reproductive to the non-reproductive stage of life. Menopause is associated with an accelerated bone loss which may lead to the development of osteoporosis in women. Vaginal dryness with its sequelae, such as urogenital infections and impaired sex life, are well known problems of menopause. The incidence of urinary tract infections increases in women with increasing age.

Correlation Between Endocrine Changes and Symptoms of the Reproductive Senescence As one of the first signs of the impending transition to menopause, in middle aged regularly menstruating women, the frequency of LH pulses decreases and the width of the peak increases before any change in the amount of plasma estradiol [11]. These changes are accompanied by elevated FSH concentrations during the early follicular phase [12] [13] [14].

Following, on the one hand there is a continuous increase of serum PSH and LH, while on the other hand a concomitant decrease in estradiol and estrone can be observed, as yearly examinations of women have shown during the transition from the reproductive to the non-reproductive stage of life [15]. Initial symptoms of the reproductive senescence, such as hot flushes and sweating, already occur in normocycling women and were significantly associated with high levels of FSH and LH and with low levels of estradiol [16]. Exacerbation of the symptoms was consistent with changes in gonadotropin levels [17] [18].

Urinary Incontinence in Women

Urinary incontinence also affects many women of all age groups. The prevalence of incontinence has been estimated to be between 9 and 74% [19] [20] [21] [22] [23] [≅] [25].

Until now, the etiology of urinary incontinence is not elucidated, but most likely is caused by several factors. Different studies have shown a correlation between the risk of urinary incontinence and age [26], number of births [20], age of giving birth [25], body mass index [23] [25], race [23] level of education [25], frequency of bed-wetting during childhood [25], physical exercise or menopausal estrogen deficiency [12]. With the development of menopause the frequency of lower urinary tract symptoms, such as urgency, hesitancy and frequency, seem to increase. [27]

The difference of the mean maximum urethral closure pressure is 20 cm $H_2O$ between continent and incontinent women of corresponding age. The closure function of the urethra deteriorates in an age dependent relationship in a similar way in continent as well as incontinent women, but is based on different initial values [28] [29] [2] [30].

Urinary incontinence predisposes to urinary tract infections, pressure ulcers, perineal rashes, and urosepsis.

4. Comparison of the Reproductive Senescence in Women and the Side Effects of Spaying in the Bitch The symptoms associated with reproductive senescence in women have amazing similarities with the side effects of spaying in the bitch. In both species there is an increased incidence of vaginal dryness, mood and behavioral changes, and urinary incontinence. A characteristic feature of urinary incontinence in women, as well as in dogs, is a reduced urethral closure function. In the bitch, spaying is proven to be the trigger for urinary incontinence.

Until now, neither the pathophysiological correlation between spaying and urinary incontinence in the bitch nor the cause of urinary incontinence in women is elucidated. But it can be assumed that similar mechanisms are involved, because for conservative treatment the same substances are recommended in both species.

In reproductive senescence in women as well as after spaying of bitches the levels of FSH and LH increase many times. Because LH receptors are not limited to the genital tract [31] [32] but are also found, among others, in the urinary bladder [33] and the skin [34], a correlation between the increased FSH- and LH levels and the clinical changes after menopause or spaying is most likely. In post menopausal women the number of LH receptors in the bladder decreases, most likely because of a down-regulation of the LH receptors by increased gonadotropin levels [33]. A down-regulation of receptors is also known to occur on a higher level, for example the pituitary gland. Prolonged exposure of GnRH receptors to GnRH results in loss of responsiveness to the hormone, through receptor alteration [35]. The outcome of such a down-regulation of sensitivity to GnRH results in a suppression of circulating levels of gonadotropins [36] [37] [38] [39] [40] [41].

Despite recent progress in understanding the pathophysiology of urinary incontinence, successful management continues to be a challenge. Medical treatment for urinary incontinence in women, or urinary incontinence in the bitch, include estrogen and/or progesterone replacement, supplementation with alpha-adrenergic agonists, beta-adrenergic receptor blocking agents, cholinergic receptor blocking compounds, cholinergic receptor stimulating drugs, nitric oxide synthase substrates, nitric oxide donors or both. Other treatment procedures include behavioral therapy, nerve stimulation, injection therapy, mechanical devices [42] [43] and surgery.

The hitherto existing medical treatments for incontinence have either unsatisfactory success or show severe side effects and can therefore not be administered to patients with e.g. glaucoma, hypertonia and cardiac arrhythmias. Therefore there exists a great need in effective pharmaceutical compositions and medicaments for the successful treatment or prevention of incontinence in female mammals with minimal adverse effects on the treated individual.

It has now surprisingly been found that a compound, or a pharmaceutical composition comprising a compound that modulates the level of biologically active gonadotropins is an effective medicament for the treatment or prevention of urinary incontinence in female mammals.

DISCLOSURE OF THE INVENTION

Hence it is an object of the present invention to use at least one GnRH analogue for the preparation of a medicament for the treatment and/or prevention of side effects of ovarectomy or symptoms associated with reproductive senescence in female mammals.

The term GnRH analogue as used herein encompasses GnRH agonists and GnRH antagonists. A GnRH antagonist is a compound which suppresses the activity of GnRH by e.g. binding the GnRH receptors on target cells and thereby blocking its biological activity or which decreases the production/release of endogenous GnRH. A GnRH agonist is a compound leading to a temporary overproduction of gonadotropins which leads to a downregulation of at least one gondadotropin i.e. FSH and/or LH.

The term GnRH analogue comprises compounds such as e.g. antibodies against GnRH and compounds leading to a cessation of GnRH production due to the use of a specific antisense gene construct.

Said GnRH analogue is preferably selected from the group consisting of peptides, polypeptides and proteins.

Side effects and symptoms in the scope of the present invention comprise vasomotor symptoms, especially hot flushes, mood changes, such as e.g. depression and aggressivity, skin changes, hair changes, and in particular urinary incontinence.

For specific treatments, a medicament of the present invention may comprise at least one further active compound selected from the group consisting of: an estrogenic agent, a partial estrogenic agent, a progestational agent, alpha adrenergic agonist, beta-adrenergic receptor blocking agent, cholinergic-receptor blocking compound, cholinergic-receptor-stimulating drug, smooth muscle relaxant, nitric oxide substrate, nitric oxide donor, and mixtures thereof.

A medicament comprising a second and/or further active compound may be, and preferably is, a combination of specific dosage units, comprising a first dosage form for the GnRH analogue, e.g. a slow release dosage form, and at least one further dosage form comprising one or more further active compounds, whereby said first and said second dosage form may be administered at the same, or at different times, and with the same or different frequencies.

In another aspect, the present invention relates to a method for the treatment and/or prevention of side effects of ovarectomy or symptoms associated with reproductive senescence in female mammals, in particular incontinence, said method comprising the administration of a composition or a medicament of the present invention to an individual in need thereof.

Upon further studies of the specification and appended claims, further aspects, objects and advantages of this invention will become apparent to those skilled in the art.

MODES FOR CARRYING OUT THE INVENTION

Thus, this invention relates to the use of a GnRH analogue for the preparation of a medicament for treating and/or preventing side effects of ovarectomy or symptoms associated with reproductive senescence, in particular urinary incontinence and vasomotor symptoms, in female mammals, in particular women and bitches.

Preferably, the amount of said at least one GnRH analogue is effective to improve the side effects of ovarectomy or symptoms associated with reproductive senescence, in particular urinary incontinence or vasomotor symptoms, by changing the pulsatile and tonic pattern of FSH and/or LH release and/or lowering the blood-level of circulating FSH and/or LH in a female mammal to whom the composition is administered.

By the methods of the present invention side effects of ovarectomy or symptoms associated with reproductive senescence, in particular urinary incontinence and vasomotor symptoms, in female mammals, in particular women and bitches, which are manifesting the symptoms thereof, can be treated and prevented.

Because the conditions of reproductive senescence and the side effects of ovarectomy are produced or aggravated by changes in the pulsatile patterns of FSH and LH and/or elevated FSH and/or LH-levels, one or more compounds leading to a decreased synthesis or a decreased release of said hormones such as e.g. deslorelin, goserelin, buserelin, triptorelin, leuprolid or their acetates or a combination of these are useful for ameliorating the side effects of ovarectomy or symptoms associated with reproductive senescence.

In certain cases an additive effect can be achieved and the severity of the symptoms can be decreased when a estrogenic agent is administered concurrently with said GnRH analogue. In the case of a female mammal, an estrogen or a progestin can be administered, or an estrogen can be administered concurrently with a progestin.

In other cases an additional effect can be achieved and the severity of the symptoms can be decreased when said at least one GnRH analogue is administered either with estrogen or progestin and supplemented with at least one compound selected from the group consisting of: alpha-adrenergic agonists, beta-adrenergic receptor blocking agents, cholinergic receptor blocking compounds, cholinergic receptor stimulating drugs, smooth muscle relaxants, nitric oxide substrates and/or nitric oxide donor receptors.

Thus, the method aspects of this invention and the medicament aspects of this invention employ one or more GnRH analogue and optionally one or more of, e.g. an estrogen (e.g. Progynova, Schering) or a progestin (e.g. progesterone, norgestrel, proligeston, medroxypro-gesteronacetate, chlormadinaonacetate), with or without at least one compound selected from the group consisting of: alpha-adrenergic agonists, beta-adrenergic receptor blocking agents, cholinergic receptor blocking compounds, cholinergic receptor stimulating drugs, smooth muscle relaxants, nitric oxide substrates and/or nitric oxide donor receptors.

Examples of typical substances leading to a decreased blood concentration of FSH and LH are:

Deslorelin acetate, Goserelin acetate, Nafarelin acetate, Buserelin acetate, Triptorelin acetate, Gonadorelin acetate, Leuprolid acetate, Danazolum, and Cetrorelix.

The amounts may be in the range known for down-regulation of LH/FSH, whereby the amount depends e.g on the formula, the intervals, the root of administration and the responsiveness of the individual. For example Deslorelin acetate usually is administered to bitches in amounts of 1 to 100 mg, preferably 3 to 20 mg at intervals from 1 month to 2 years. The amount depends on the dog's size, whereby the amount usually is at least about 0.1 mg/kg, preferably at least 5 mg/kg.

Substances leading to a decreased concentration of Follicle stimulating hormone (FSH) and/or Luteinizing hormone (LH) and/or to a decreased or increased concentration or activity of Gonadotropin releasing hormone (GnRH) can be administered preferentially by a subcutaneous or intramuscular implant.

Examples of second or further active agents, or combinations thereof which can be administered concurrently with a GnRH analogue are estrogens, partial estrogen agonists (partial estrogens), and progestins.

Estrogens and/or partial estrogens and/or progestins—if any—are usually administered to supplement endogenous production, the amount of estrogen being bioequivalent to approximately 0.005 mg-2 mg per day of estradiol (e.g. Progynova, Schering), the amount of a partial estrogen being bioequivalent to approximately 0.002 mg-200 mg per day of e.g. raloxifene, and the amount of the progestational agent administered being bioequivalent to 50-300 mg of injected progesterone.

Estrogens may e.g. be administered as estradiol, estradiol valerate, estradiol hemihydrate, vaginal estradiol tablets, vaginal estradiol creams and/or vaginal estradiol rings.

Partial Estrogen Agonists (partial estrogens) are e.g. raloxifene, tamoxifen, nafoxidin, centchroman, and toremifen.

Further optionally present agents include:
Alpha-adrenergic-receptor-agonists, e.g. Phenylpropanolamine and Phenylephrine;
Beta-receptor-blocking agents, e.g. Propranolol, Befaxolol, Acebutolol, Atenolol, and Bisoprolol;
Cholinergic-receptor blocking compounds, e.g. Benztropine, Biperiden, and Propantheline;
Cholinergic-stimulating drugs, e.g. Bethanecol and Nitroglycerine.

Combinations of smooth muscle relaxants and anticholinergics may also be present and comprise e.g. oxybutynin, dicyclomine, and flavoxate. Such smooth muscle relaxants, may be combined with e.g. anticholinergics and α-adrenergics such as imipramine and/or desipramine.

Many other examples of compounds in each of the foregoing categories are well known and can be employed in this invention in the above described combination.

A GnRH analogue can be administered either alone, or in combination with other active substances, in admixture with conventional excipients, i.e., pharmaceutically acceptable liquid, semi-liquid or solid organic or inorganic carriers, in particular carriers suitable, e.g., for parenteral or enteral application. It goes without saying that such carriers are much preferred that do not deleteriously react with the active compound in admixture therewith. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be and preferably are sterilized. The pharmaceutical preparations can—if desired—be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application particularly suitable are solutions, preferably oily or aqueous solutions, as well as suspensions, emulsions, or implants, including transdermal patches, and vaginal gels, creams and foams. Ampoules are convenient unit dosages. Another suitable dosage form, especially for long lasting effects, are microencapsulated drugs.

For enteral application, particularly suitable are unit dosage forms, e.g. for rectal application suppositories, for oral application tablets, dragees, capsules or, having talc and/or carbohydrate carrier or binder or the like, the carrier preferably being lactose and/or corn starch and/or potato starch; particulate solids, e.g., granules; and liquids and semi-liquids, e.g., syrups and elixirs or the like, wherein preferably a sweetened vehicle is employed. Sustained release compositions can be formulated including those wherein the active compound is protected with differentially degradable coatings, e.g., by microencapsulation, multiple coatings, etc.

Suitable for oral administration are, inter alia, tablets, dragees, capsules, pills, granules, suspensions and solutions.

As already mentioned above, a GnRH analogue can be administered as an admixture with an estrogen and/or partial estrogen and/or progestational agent and/or any other optional active agent, or it can be administered as a separate unit dosage form, either simultaneously with a unit form of a second and/or further active compound at the same time or at different times during a day, or at different days, and with the same or different intervals.

For administration by injection or implant the active agents are preferably formulated as slow release formulations which deliver the active agents continuously. Such formulations may be designed for different frequencies of administration such as once a day, once a week, once a month, once all six months, once a year, or even for administration at larger intervals, whereby administration once all six months to once a year is presently preferred.

If administration by injection or implant at intervals of e.g. six months to one year is chosen for the GnRH analogue, a second or further active substance may be administered at shorter intervals, e.g. in the form of tablets thereby allowing easy adaptation of the dosage of one such substance or the sequential administration of different substances in the same or different dosages, e.g. to better react on naturally occurring hormonal changes. The frequency of such administration of a second and/or further active substance may e.g. be once a day, once a week, once a month etc.

In mammals, suitable ratios at which an at least one GnRH analogue should preferably produce in humans FSH and LH blood plasma levels <3 IU/l or <6 IU/l respectively.

BRIEF DESCRIPTION OF THE EXPERIMENTS

Fifteen bitches suffering from urinary incontinence after spaying, which did not respond to or tolerate an other incontinence treatment before, such as a treatment with ephedrine, estrogen, flavoxate, phenylpropanolamine or collagen deposits, were first clinically examined and thereafter a GnRH analogue in a dosage of 3.75-12 mg, in slow release form, was subcutaneously implanted between the shoulder blades. Additionally, for a limited period the dogs were treated with phenylpropanolamine in a dosage of 1.5 mg/kg BW tid orally. Combined treatment completely resolved the incontinence in 12 bitches and in one bitch the incontinence was significantly less severe. Only two dogs out of fifteen did not respond with an improvement in continence, whereby one of said dogs was treated with an amount below the proposed minimal dosage.

After discontinuation of the shortacting phenylpropanolamine 8 bitches remained continent. Their continence was therefore achieved solely by the treatment with the composition as described in the present invention. Seven out of fifteen dogs seemed to be much happier and in none of the dogs did the general condition deteriorate. Three dogs, which were aggressive against other dogs before the treatment, were less aggressive against other dogs after the treatment. The respective results are shown in more detail in table 1.

In a second ongoing study, 16 client owned dogs suffering from urinary incontinence were enrolled in a double-blind, placebo-control study. In the initial phase of the study, dogs were randomly assigned to treatment with a long-acting GnRH analogue (leuprolide acetate) or placebo (dog owners and the investigators were blinded to treatment) along with a short course of therapy with phenylpropanolamine. 5 weeks after treatment with drug or placebo, dogs were evaluated and, if not fully continent, treated with a long-acting GnRH analogue (leuprolide acetate) in an open label phase of the study. To date only 1 of 10 dogs treated with placebo became continent vs. 3 to 8 dogs treated with drug during the blinded portion of the study. Overall, the results generated thus far indicate 6 of 15 dogs treated with the long-acting GnRH analogue became continent and 9 of the remaining dogs improved after discontinuation of the short acting phenylpropanolamine. Only 1 dog of 15 treated with the GnRH analogue was considered not to have improved following treatment with the drug.

Two cocker spaniel bitches belonging to the same owner were showing excessive growth of the undercoat due to spaying. One of theses dogs did not tolerate estrogen treatment before. Both dogs were first clinically examined and thereafter a GnRH analogue (Deslorelin) in a dosage of 5 mg, in slow release form, was subcutaneously implanted between the shoulder blades. 5 weeks after the injection an obvious amelioration of the coat quality was seen in both dogs, 21 weeks after injection no signes of "baby coat" were apparent anymore.

As use in humans is concerned, a perimeno-pausal woman with urge incontinence and hotflushes reported both symptoms improved considerably for a period of about 4 weeks after treatment with 3.75 mg triptorelinacetate. A second menopausal woman, suffering from stress incontinence for at least 6 years, was treated with a single dose of 3.75 mg of leuprolide acetate. 24 hour pad tests conducted prior to treatment with the drug indicated she lost between 10 and 130 ml of urine on a daily basis due to her incontinence. A pad test conducted 2 weeks after treatment with leuprolide acetate indicated daily urine loss had decreased to only 1 ml of urine and the patient claimed to be very satisfied with the effects of the therapy.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

TABLE 1

| dog weight (kg) | Duration of incontinence prior to treatment | Other problems | Treatment | Side effects | Effect on incontinence | Duration of effect after treatment | Comments |
|---|---|---|---|---|---|---|---|
| 44 | 2 years | No | 6 mg Deslorelinacetate | — | 100% | >344 d | |
| 28 | 10 months | Atopy | 6 mg Deslorelinacetate | More playfull | 100% | >340 d | |
| 6 | 2 years | Too short urethra | 6 mg Deslorelinacetate | | with PPA 100% | >336 d | |
| 28 | 4 years | Timid | 12 mg Deslorelinacetate | More self-assured | with PPA 80% | 135 d | Collagen |
| 60 | 2, 3 years | Cardiomyopathy, Vaginitis | 12 mg Deslorelinacetate | — | 100% | 64 d | Euthanatized osteosarcoma |
| 28 | 2 years | proteinuria | 12 mg Deslorelinacetate | — | 100% | >64 d | |
| 32 | 5 years | — | 12 mg Deslorelinacetate | | with PPA 100% | >318 d | |
| 20 | 2 years | Isosthenuria, polydipsia | 12 mg Deslorelinacetate | More tolerant against males | with PPA 100% | >225 d | |
| 40 | 1 months | Aggressive | 12 mg Deslorelinacetate | less aggressive more activ | 100% | >209 d | |
| 36 | 4 months | polydipsia, timid | 3,75 mg Triptorelinacetate * | — | Not effective | 0 | * dose too low |
| 60 | 2 years | | 6,3 mg Buserelinacetate | — | 100% | 44 d | |
| 28 | 2 years | sebaceous adenitis epilepsia | 6,3 mg Buserelinacetate | agile, more playfull | 100% | 83 d | |
| | | | 6 mg Deslorelinacetate | agile, more playfull | 100% | >47 d | |
| 30 | 1, 5 years | | 11,25 mg Leuprorelinacetate | Better mood | Not effective | 0 | |

TABLE 1-continued

| dog weight (kg) | Duration of incontinence prior to treatment | Other problems | Treatment | Side effects | Effect on incontinence | Duration of effect after treatment | Comments |
|---|---|---|---|---|---|---|---|
| 25? | 4 months | proteinuria | 11,25 mg Leuprorelinacetate | Less aggressiv | with PPA 100% | >64 d | |
| 18? | 21 months | | 11,25 mg Leuprorelin acetate | — | 100% | >14 d | |

REFERENCES

1. Society, I. C. *First report on the standardization of terminology of lower urinary tract*, Br J Urol, 1976. 48: p. 39-42.
2. Hilton, P. and S. L. Stanton, *Urethral pressure measurement by microtransducer: the results in symptom-free women and in those with geniune stress incontinence.* Brit J Obstet Gynaecol, 1983. 90: p. 919-933.
3. Arnold, S., *Harninkontinenz bei kastrierten Hündinnen: Bedeutung, Pathophysiologie und Behandlung.* Vet special, ed. F. E. Verlag. 1997, Stuttgart: Ferdinand Enke Verlag. P.1-103.
4. Ballanger, P. and P. Rischmann, *Female urinary incontinence.* Eur Urol, 1999. 36: p. 165-174.
5. Colon, J. et al., Effects of contraceptove doses of the progestagen megestrol acetate on luteinizing hormone and follicle-stimulating hormone secretion in female dogs. J Reprod Fert, 1993. Suppl 47: p. 519-521.
6. Arnold, S., et al., *Incontinentiae urinae bei der kastrierten Hündin: Häufigkeit und Rassedisposition.* Schweiz Arch Tierheilk, 1989. 131: p. 259-263.
7. Hodkinson, C. P. and S. L. Stanton, Retropubic urethropexy or colposuspension. In: S. L. Stanton & E. A. Tanagho (ed): Surgery of female incontinence. Berlin: E. A. Springer Verlag, 1980.55-68.
8. Holt, P. E., *Urinary incontinence in the bitch due to sphincter mechanism incompetence: surgical treatment.* J Small Anim Pract 1985. 26: 237-246.
9. Holt, P. E., *Long-term evaluation of colposuspension in the treatment of urinary incontinence due to incompetence of the urethral sphincter mechanism in the bitch.* Vet Rec, 1990. 127: p.537-542.
10. Wise, P. M., K. M. Krajnak, and M. L. Kashon, *Menopause: The aging of multiple pacemakers.* Science, 1996. 273: p.67-70.
11. Ushiroyama, T., et al., *Hypergonadotropinemia with estradiol secretion in peri- and post-menopausal period.* Acta Obstet Gynecol Scand, 1989. 68: 139-143.
12. Sherman, B. M., J. H. West and S. G. Korenman, *The menopausal transition: Analysis of LH, FSH, Estradiol and Progesterone Concentrations during menstrual cycles of older women.* J Clin Endocrin Metab, 1976. 42: p. 629-636.
13. Lenton, E. A. et al., *Inhibin concentrations throughout the menstrual cycles of normal, infertile, and older women compared with those during spontaneous conception cycles.* J Clin Endocrinol Metabol, 1991. 73: p. 1180-1190.
14. MacNaughton J. et al., *Age related changes in follicle stimulating hormone, luteinizing hormone, oestradiol and immunoreactive inhibin in women of reproductive age.* Clin Endocrinol, 1992. 36:339-45.
15. Overlie, I., et al., *The endocrine transition around menopause—a five years prospective study with profiles of gonadotropines, estrogens, androgens and SHEG among healthy women.* Acta Obstet Gynecol Scand, 1999. 78: p. 642-647.
16. Larson, B., A. Collins, and B. M. Landgren, *Urogenital and vasomotor symptoms in relation to menopausal status and the use of hormone replacement therapy (HRT) in healthy women during transition to menopause.* Maturitas, 1997. 28(2): p. 99-105.
17. Ushiroyama, T., K. Toyoda, and O. Sugimoto, *Contribution of endocrine changes to depressive mood in per- and post-menopausal women.* Bulletin of the Osaka Medical College, 1991. 37: p. 81-86.
18. Ushiroyama, T., et al., *Correlation between climateric disorder and endocrine features-longitudinal study for climateric women with symptoms.* Adv in Obsterics and Gynecology, 1991. 43: p. 202-206.
19. Mohide, E. A., *The prevalence and scope of urinary incontinence.* Chin Geriatr Med, 1986. 2(4): p. 639-654.
20. Jolley, J. V., *Reported prevalence of urinary incontinence general practice.* Br Med J, 1988. 297: p. 1300-1302.
21. Versi, E., *Incontinence in climateric.* Clin Obstet Gynecol, 1990. 33(2): p. 392-398.
22. Herzog, A. R. and N. H. Fultz, *Prevalence and incidence of urinary incontinence in community-dwelling population.* J Am Geriatr Soc, 1990. 38(3): p. 273-281.
23. Burgio, K. L. and B. T. Engel, *Prevalence, incidence and correlates of urinary incontinence in healthy, middle-aged women.* J Urol, 1991. 146: p. 1255-1259.
24. O'Conell, H. E., R. J. MacGregor, and J. M. Rusell, *Female urinary incontinence management in healthy, middle aged women.* J Aust, 1992. 157(8): p. 537-544.
25. Kuh, D., L. Cardozo, and R. Hardy, *Urinary incontinence in middle aged women: childhood enuresis and other lifeteime risk factors in a British prospective cohort.* J Epidemiol Community Health, 1999. 53(8): p. 453.
26. Yarnell, J. W. G. and A. S. St. Leger, *The prevalence, severity and factors associated with urinary incontinence in a random sample of the elderly.* Age Ageing, 1979. 8: p. 81.
27. Cervigni, M., *Hormonal influences in the lower urinary tract.* Female urology, ed. S. Raz. 1996, Philadelphia: Saunders, W. B. 539-559.
28. Rud, T., *Urethral pressure profile in continent women from childhood to old age.* Acta OBstet Gynecol, 1980. 59: p. 331-335.
29. Edwards, L. and J. Malvern, *The urethral pressure profile: Theoretical considerations and clinical application.* British J Urol, 1974. 46: p. 325-336.
30. Abrams, P, R. C. L. Feneley and M. Torrens. *Klinischer Wert urodynamischer Untersuchungen.* In: P. Abrams, R. C. L. Feneley and M. Torrens (eds.)1987: Urodynamic für Klinik und Praxis. Berlin: Springer-Verlag, 126-186.
31. Misrahi, M., et al., *The LH/CG and FSH receptors: different molecular forms and intracellular traffic.* Molecular and cellular endocrinology, 1996. 125: p. 161-167.

32. Wasowicz, G., et al., *Evidence for the presences of luteinizing hormone-chorionic gonadotrophin receptors in the pig umbilical cord.* Journal of reproduction and fertility, 1999. 117: p. 1-9.
33. Tao, Y.-X., et al., *The urinary bladder of a women is a novel site of luteinizing hormone-human chorionic gonadotropin receptor gene expression.* Am J Obstet Gynecol, 1998. 179(4): p. 1026-1031.
34. Venencie, P. Y., et al., *Luteinizing hormone/human chorionic gonadotrophin receptors in various epidermal structures.* British Journal of Dermatology, 1999. 141: p. 438-446.
35. Hazum, E. and P. M. Conn, Molecular mechanism of gonadotropin releasing hormone (GnRH) Action. I. The GnRH Receptor. Endocrine Review, 1988. 9: p. 379-856.
36. Cavitte, J.-C., et al., *Reversible effects of long-term treatment D-TRP6-LH-RH on pituitary gonadal axis, spermatogenesis and prostate morphology in adolescent and adult dogs.* Andrologia, 1988. 20: p. 249-263.
37. Lacoste, D., et al., *Normal gonadal functions and fertility after 23 months of treatment of pre-pubertal male and female dogs with the GnRH agonist (D-Trp6, des-Gly-NH102)GnRH etylamide.* J Androl, 1989. 10: p. 456-465.
38. Lacoste, D., et al., *Reversible inhibition of testicular androgen secretion by 3-, 5- and 6 month controlled release microsphere formulations of the LH-RH agonist (D-Trp6, des-Gly-NH102)LH-RH ethylamide in the dog.* J Steroid Biochem, 1989. 33: p. 1007-1011.
39. Aspden, W. J., et al., *Direct actions of the Luteinizing Hormone-Releasing Hormone Agonist, Deslorelin, on Anterior Pituitary contents of Luteinizing Hormone (LH) and Follicle-Stimulating Hormone (FSH), LH and FSH subunit messenger ribonucleid acid, and Plasma concentrations of LH and FSH in castrated male cattle.* Biology of reproduction, 1996. 55: p. 386-392.
40. Roger, M., et al., Long term treatment of male and female precocious puberty by periodic administration of a long-acting preparation of D-Trp6-Luteinizing hormone-releasing hormone microcapsules. Journal of Clinical Endocrinology and Metabolism, 1986. 62(4): p. 670-677.
41. Okkens, A. C., et al., Evidence for prolactin as the main luteotrophic factor i the cycle of the dog. The veterinary quarterly, 1990. 12(4): p. 193-201.
42. Kobashi, K. C. and G. E. Leach, *Stress urinary incontinence.* Curr Opin Urol, 1999. 9(4): p. 285-290.
43. Glavind, K., A. L. Mouritsen, and G. Lose, *Management of stress and urge urinary incontinence in women.* Acta Obstet Gynecol Scand, 1999. 78: p. 75-81.

The invention claimed is:

1. A method for the treatment of urinary incontinence in a female mammal in need thereof comprising administering an effective amount of at least one GnRH analogue to said female mammal wherein said GnRH analogue is deslorelin acetate, goserelin acetate, nafarelin acetate, buserelin acetate, triptorelin acetate, gonadorelin acetate, leuprolid acetate, Cetrorelix or mixtures thereof.

2. A method according to claim 1 wherein at least said GnRH analogue is administered in a slow release formulation.

3. A method according to claim 1 wherein said treatment consists essentially of administering at least one GnRH analogue.

4. A method according to claim 1 wherein said female mammal is a human female pre-or postmenopausal, or a female dog.

5. A method according to claim 1 wherein said at least one GnRH analogue is administered as part of a formulation for subcutaneous administration.

6. A method according to claim 1 wherein said at least one GnRH analogue is administered as part of a formulation for parenteral, oral or rectal administration.

7. A method according to claim 1 wherein said at least one GnRH analogue is administered as part of a formulation for intranasal, transdermal or intravaginal administration.

8. A method according to claim 1 wherein said at least one GnRH analogue and a further active substance are administered in different unit forms.

9. A method according to claim 1 wherein a further active substance is administered to said female mammal, and wherein said substance is selected from the group consisting of an estrogenic agent, a partial estrogenic agent, a progestational agent and mixtures thereof.

10. A method according to claim 9 wherein said estrogenic agent is estradiol valerate, a conjugated equine estrogen, 17β-estradiol, estrone or estriol; the partial estrogenic agent is raloxifene, centchroman, toremifen or tamoxifen; and the progestational agent is progesterone, hydroxygesterone, medroxyprogesterone, norethisterone, levonogestrel, norgestrel, gestodene or drospirenone.

11. A method according to claim 1 wherein a further active substance is administered to said female mammal, and wherein said active substance is alpha-adrenergic agonist, beta adrenergic receptor blocking agent, cholinergic receptor blocking compound, cholinergic receptor stimulating drug, smooth muscle relaxant, nitric oxide synthase substrate, a nitric oxide donor, or a mixture thereof.

12. A method for reducing the risk of urinary incontinence in a female mammal in need thereof comprising administering an effective amount of at least one GnRH analogue to said female mammal wherein said GnRH analogue is deslorelin acetate, goserelin acetate, nafarelin acetate, buserelin acetate, triptorelin acetate, gonadorelin acetate, leuprolid acetate, Cetrorelix or mixtures thereof.

13. A method according to claim 12 wherein a further active substance is administered to said female mammal, and wherein said substance is selected from the group consisting of an estrogenic agent, a partial estrogenic agent, a progestational agent and mixtures thereof.

14. A method according to claim 13 wherein said estrogenic agent is estradiol valerate, a conjugated equine estrogen, 17β-estradiol, estrone or estriol; the partial estrogenic agent is raloxifene, centchroman, toremifen or tamoxifen; and the progestational agent is progesterone, hydroxygesterone, medroxyprogesterone, norethisterone, levonogestrel, norgestrel, gestodene or drospirenone.

15. A method according to claim 12 wherein a further active substance is administered to said female mammal, and wherein said active substance is alpha-adrenergic agonist, beta adrenergic receptor blocking agent, cholinergic receptor blocking compound, cholinergic receptor stimulating drug, smooth muscle relaxant, nitric oxide synthase substrate, a nitric oxide donor, or a mixture thereof.

16. A method according to claim 12 wherein at least said GnRH analogue is administered in a slow release formulation.

17. A method according to claim 12 wherein said female mammal is a human female pre-or postmenopausal, or a female dog.

18. A method according to claim 9 wherein said at least one GnRH analogue and said further active substance are administered in different unit forms.

* * * * *